United States Patent [19]

Poser et al.

[11] Patent Number: 5,968,253
[45] Date of Patent: Oct. 19, 1999

[54] CALCIUM PHOSPHATE CEMENTS COMPRISING ANTIMICROBIAL AGENTS

[75] Inventors: Robert Poser, Scotts Valley; Mark Fulmer, San Jose; Brent R. Constantz, Portola Valley, all of Calif.

[73] Assignee: Norian Corporation, Cupertino, Calif.

[21] Appl. No.: 09/127,996

[22] Filed: Jul. 31, 1998

[51] Int. Cl.$^6$ .......................... C04B 12/02; A61K 33/06
[52] U.S. Cl. ...................... 106/691; 106/15.05; 106/35; 106/690; 423/305; 423/307; 424/422; 424/484; 424/602; 424/603; 433/228.1; 606/76; 623/16
[58] Field of Search .......................... 106/35, 690, 691, 106/15.05; 424/422, 484, 602, 603, 93.4, 93.43; 606/76; 623/16; 433/228.1; 423/305, 307

[56] References Cited

U.S. PATENT DOCUMENTS

| | | | |
|---|---|---|---|
| 4,108,690 | 8/1978 | Heller | 148/263 |
| 4,587,268 | 5/1986 | Pfirrmann | 514/774 |
| 4,684,673 | 8/1987 | Adachi | 523/116 |
| 4,772,468 | 9/1988 | Pfirrmann | 424/128 |
| 4,880,610 | 11/1989 | Constanz | 423/305 |
| 5,037,639 | 8/1991 | Tung | 424/57 |
| 5,047,031 | 9/1991 | Constanz | 606/77 |
| 5,053,212 | 10/1991 | Constanz et al. | 423/305 |
| 5,129,905 | 7/1992 | Constanz | 606/76 |
| 5,151,122 | 9/1992 | Atsumi et al. | 106/35 |
| 5,178,845 | 1/1993 | Constanz et al. | 423/305 |
| 5,336,264 | 8/1994 | Constanz et al. | 623/16 |
| 5,468,489 | 11/1995 | Sakuma et al. | 424/49 |
| 5,496,399 | 3/1996 | Ison et al. | 106/35 |
| 5,508,342 | 4/1996 | Antonucci et al. | 524/788 |
| 5,569,442 | 10/1996 | Fulmer et al. | 423/311 |
| 5,571,493 | 11/1996 | Fulmer et al. | 423/308 |
| 5,580,623 | 12/1996 | Fulmer et al. | 428/34.1 |
| 5,591,453 | 1/1997 | Ducheyne et al. | 424/484 |
| 5,650,176 | 7/1997 | Lee et al. | 424/602 |
| 5,676,976 | 10/1997 | Lee et al. | 623/16 |
| 5,683,461 | 11/1997 | Lee et al. | 106/35 |
| 5,683,496 | 11/1997 | Ison et al. | 106/35 |
| 5,697,981 | 12/1997 | Ison et al. | 623/16 |

OTHER PUBLICATIONS

Bohner, Marc, et al., "Gentamicin–Loaded Hydraulic Calcium Phosphate Bone Cement As Antibiotic Delivery System," *Journal Of Pharmaceutical Sciences* (May 1997) vol. 86, No. (5):565–572.

Cimbollek, M., et al., "Antibiotics Impregnated Heart Valve Sewing Rings—Antibacterial Activity, Release Kinetics And Animal Pharmacokinetics," *The 20$^{th}$ Annual Meeting of the Society For Biomaterials* (Apr. 5–9, 1994) Boston, Massachusetts, USA, p. 490.

Constantz, Brent R., et al., "Skeletal Repair By In Situ Formation Of The Mineral Phase Of Bone," *Science* (Mar. 24, 1995) vol. 267:1796–1799.

Gerhart, T.N., et al., "Antibiotic–Loaded Biodegradable Bone Cement For Prophylaxis And Treatment Of Experimental Osteomyelitis In Rats," *Journal Of Orthopaedic Research* (1993) vol. 11:250–255. No Month.

Hamanishi, Chiaki, et al., "A Self–Setting TTCP–DCPD Apatite Cement For Release OF Vancomycin," *Journal Of Biomedical Materials Research* (*Applied Biomaterials*) (1996) vol. 33:139–143. No Month.

Nachiondo, J.M., et al., "Antibiotic Impregnation Of A Resorbable Calcium Phosphate Cement," *The 20$^{th}$ Annual Meeting of the Society For Biomaterials* (Apr. 5–9, 1994) Boston, Massachusetts, USA, p. 146.

Otsuka, Makoto, et al., "A Novel Skeletal Drug Delivery System Using Self–Setting Calcium Phosphate Cement. 2. Physicochemical Properties And Drug Release Rate Of The Cement–Containing Indomethacin," *Journal Of Pharmaceutical Sciences* (May 1994) vol. 83, No. (5):611–615.

Otsuka, Makoto, et al., "Drug Release From A Novel Self–Setting Bioactive Glass Bone Cement Containing Cephalexin And Its Physicochemical Properties*," *Journal Of Biomedical Materials Research* (1995) vol. 29:33–38. No Month.

Poser, Robert, et al., "Antibiotic Impregnation Of A Resorbable Calcium Phosphate Cement," *ISFR–94*, Sep. 27–Oct. 1, 1994, Kobe, Japan, p. 19.

Takechi, Masaaki, et al., "Effects Of Added Antibiotics On The Basic Properties Of Anti–Washout–Type Fast–Setting Calcium Phosphate Cement," *Journal Of Biomed. Mater Res.* (Feb. 1998) vol. 39:308–316.

Yu, Duncan, et al., "Self–Setting Hydroxyapatite Cement: A Novel Skeletal Drug–Delivery System For Antibiotics," *Journal Of Pharmaceutical Sciences* (Jun. 1992) vol. 81, No. (6):529–531.

Chemical Abstract No. 103:166174, abstract of Japanese Patent No. 60–103963, Jun. 1985.

Chemical Abstract No. 121:91861, abstract of Japanese Patent Specification No. 06–135840, May 1994.

Chemical Abstract No. 126:162142, abstract of an article by Trecant et al entitled "Dynamic Compaction: A new process to compact therapeutic agent–loaded calcium phosphates", Biomaterial, 18(2), 141–145, 1997 No Month.

Chemical Abstract No. 127:86015, abstract of an article by Radin et al entitled "Calcium phosphate ceramic coatings as carriers of vancomycin", Biomaterials, 18(11), 777–782, 1997 No Month.

(List continued on next page.)

*Primary Examiner*—Anthony Green
*Attorney, Agent, or Firm*—Bozicevic, Field & Francis LLP; Bret Field

[57] ABSTRACT

A flowable, paste-like composition capable of setting in a clinically relevant period of time into an antimicrobial agent loaded apatitic product having sufficient compressive strength to serve as a cancellous bone structural material is provided. The subject compositions are prepared by combining dry ingredients with a physiologically acceptable lubricant and an antimicrobial agent, where the dry ingredients comprise at least two different calcium phosphates. The subject compositions find use in a variety of different applications, including orthopaedic, dental and craniomaxillofacial applications.

29 Claims, 1 Drawing Sheet

OTHER PUBLICATIONS

Chemical Abstract No. 128:26952, abstract of PCT International Application No. 9741842, Nov. 1997.

European Patent Abstract No. EP000540819A1, abstract of European Patent Specification No. 540819, May 1993.

JAPIO Patent Abstract No. JP362019507A, abstract of Japanese Patent Specification No. 62–019507, Jan. 1987.

JAPIO Patent Abstract No. JP403267067A, abstract of Japanese Patent Specification No. 03–267067, Nov. 1991.

WPIDS Abstract No. 93–378243, abstract of German Patent Specification No. 4216496, Nov. 1993.

WPIDS Abstract No. 94–071797, abstract of Japanese Patent Specification No. 06–0249191, Feb. 1994.

CALCIUM PHOSPHATE CEMENTS COMPRISING ANTIMICROBIAL AGENTS

FIELD OF THE INVENTION

The field of the invention is calcium phosphate cements.

BACKGROUND

Calcium phosphate cements, in which one or more dry components and a liquid are combined to form a flowable, paste-like material that is subsequently capable of setting into a solid calcium phosphate product, hold great promise for use as structural materials in the orthopedic, craniomaxillofacial, dental and related fields. For example, it is desirable to be able to inject a flowable material into a cancellous bone void and have the material set into a solid calcium phosphate mineral product that is capable of withstanding physiological loads. Materials that set into solid calcium phosphate mineral products are of particular interest as such products can closely resemble the mineral phase of natural bone and are potentially remodelable, making such products extremely attractive for use in orthopedics and related fields.

In view of the great interest in calcium phosphate cements, a variety of different formulations have been developed to date. See the Relevant Literature section infra.

Despite the number of different calcium phosphate cements that have been produced, there is continued interest in the development of new calcium phosphate cements that are particularly suited to a particular type of application. One such cement of interest would be a calcium phosphate cement that produces a flowable material capable of setting into an antimicrobial apatitic product that is suitable for use a cancellous bone structural material.

Relevant Literature

U.S. Pat. No. 5,591,453 describes a silica-based glass carrier for biologically active molecules. Patents of interest describing calcium phosphate cements include: 4,684,673; 5,037,639, 5,683,461; 5,676,976; 5,650,176; 4,108,690 and 5,508,342, as well as 4,880,610; 5,047,031; 5,129,905; 5,336,264; 5,053,212; 5,178,845; 5,580,623; 5,569,442; 5,571,493; 5,496,399; 5,683,667; 5,683,496; and 5,697,981. Also of interest are WO 96/36562 and WO 97/17285.

Constantz et al., "Skeletal Repair by in Situ Formation of the Mineral Phase of Bone," Science (Mar. 24, 1995) 267: 1796–1798, describes a calcium phosphate cement comprising α-tricalcium phosphate, MCPM, and $CaCO_3$. Also of interest is: Lemaitre et al., "Setting, Hardening and Resorption of Calcium Phosphate Hydraulic Cements," Rev. Stomatol. Chir. Maxillofac. (1992) 93: 163–165.

Other references of interest include: Takechi et al., "Effects of Added Antibiotics on the Basic Properties of Anti-Washout-Type Fast-Setting Calcium Phosphate Cement," J. Biomed. Mater. Res. (February 1998) 39: 308–316; Bohner et al., "Gentamycin-Loaded Hydraulic Calcium Phosphate Bone Cement as Antibiotic Delivery System," J. Pharm. Sci. (May 1997) 86: 565–572; Hamanishi et al., "A Self-Setting TTCP-DCPD Apatite Cement for Release of Vancomycin," J. Biomed. Mater. Res. (1996) 33: 139–143; Otsuka et al., "A Novel Skeletal Drug Delivery System Using Self-Setting Calcium Phosphate Cement," J. Pharm. Sci. (November 1994) 83: 1569–1573; Otsuka et al., "A Novel Skeletal Drug Delivery System Using Self-Setting Calcium Phosphate Cement," J. Pharm. Sci. (May 1994) 83:611–615; Welch, "Antibiotics in Acrylic Bone Cement," J. Biomed Mater. Res. (1978) 12: 679–700; and Lautenschlager et al., "Mechanical Properties of Bone Cements Containing Large Doses of Antibiotic Powders," J. Biomed. Mater. Res. (November 1976) 10: 929–938.

SUMMARY OF THE INVENTION

Calcium phosphate cements comprising dry and liquid components that, upon combination, produce a paste-like product capable of setting in a clinically relevant period of time into an antimicrobial agent loaded apatitic product having a compressive strength sufficient to serve as a cancellous bone substitute material are provided. The cements have: (a) at least two different calcium phosphate sources as dry ingredients; (b) a physiologically acceptable aqueous lubricant; and (c) an antimicrobial agent. In using the subject cements, the dry and liquid components are combined to produce a flowable, paste-like material. The resultant paste-like material finds use in a variety of different applications, including orthopedic, dental and cranio-maxillofacial applications.

DESCRIPTION OF THE SPECIFIC EMBODIMENTS

Figure 1:
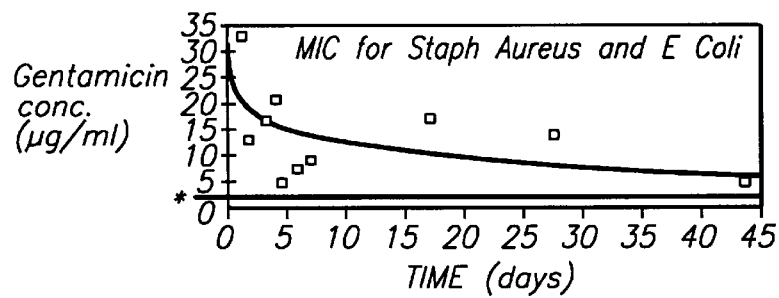
FIG. 1 provides a graph of the total amount of gentamycin released from a cement according to the subject invention, where the values are reported cumulatively at each time interval.

Calcium phosphate cements having dry and liquid components that, upon combination, produce a flowable, paste-like material capable of setting into an antimicrobial agent loaded apatitic product are provided. The subject cements comprise: (a) at least two different calcium phosphates as dry ingredients; (b) a physiologically acceptable aqueous lubricant; and (c) an antimicrobial agent. In using the subject formulations, the dry and liquid components are combined to produce a flowable, paste-like product capable of setting in situ in a clinically relevant period of time into an antimicrobial agent loaded apatitic product having a sufficient compressive strength such that it can be used as a cancellous bone structural material. The subject formulations find use in a variety of different applications, including orthopedic, dental and cranio-maxillofacial applications.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The cements of the subject invention comprise a liquid component and a dry component. Upon mixture of the two components, a flowable, paste-like composition is produced that is capable of setting in a clinically relevant period of time into an antimicrobial agent loaded apatitic product having sufficient compressive strength such that it can serve as a cancellous bone structural material. By clinically relevant period of time is meant that the paste-like composition sets in less than about 20 minutes, usually less than about 15 minutes and often in less than about 10 minutes, where the composition remains flowable for at least about 1 minute, usually at least about 2 minutes and, in many embodiments, for at least about 5 minutes following combination or mixture of the precursor liquid and dry cement components. When the paste-like composition is set, the resultant antimicrobial agent loaded apatitic product has a compressive strength that makes it suitable for use as a cancellous bone structural material, i.e. it can be used as a cancellous bone substitute material as it is capable of withstanding the physiological compressive loads experienced by compressive bone under at least normal physiological conditions. As such, the subject flowable paste-like material is one that sets into a product having a compressive strength of at least about 20, usually at least about 40 and more usually at least about 50 MPa, as measured by the in vitro assay described in the Experimental section, infra, where the compressive strength of the final apatitic product may be as high as 60 or higher, but will generally not exceed about 70 MPa. Preferably, the flowable paste like composition is capable of setting in a fluid environment, such as an in vivo environment at a bone repair site. The subject paste-like composition is preferably capable of setting into a hydroxyapatitic product, and more preferably into a carbonated hydroxyapatite, i.e. dahllite, having a carbonate substitution of from 2 to 10%, usually 2 to 8% by weight of the final product.

As mentioned above, the subject cements comprise a dry component, a liquid component and an antimicrobial agent. The dry component comprises at least two calcium phosphates as dry ingredients. Calcium phosphates of interest include: monocalcium phosphate monohydrate, monocalcium phosphate anhydrous, dicalcium phosphate anhydrous, dicalcium phosphate dihydrate, tetracalcium phosphate, tricalcium phosphates ($\alpha$, $\beta$ and $\gamma$, preferably $\alpha$), octacalcium phosphate, amorphous calcium phosphates, and the like. Preferred are those cements comprising at least an acidic calcium phosphate, e.g. monocalcium phosphate monohydrate, monocalcium phosphate anhydrous, dicalcium phosphate anhydrous, dicalcium phosphate dihydrate, and a basic calcium phosphate, e.g. tetracalcium phosphate, tricalcium phosphates, as the two calcium phosphates. In addition to the at least two different calcium phosphates, the dry component of cement may further include one or more additional calcium sources, such as $CaCO_3$, CaOH, CaO, $CaNO_3$, $CaCl_2$, $CaF_2$, Ca alginates, and the like.

In a preferred cement of the subject invention, the dry cement components include calcium carbonate, tricalcium phosphate, preferably $\alpha$-tricalcium phosphate, more preferably reactive $\alpha$-tricalcium phosphate, as described in U.S. Pat. No. 5,569,442 the disclosure of which is herein incorporated by reference, and monocalcium phosphate monohydrate, where one or more of, including all of, these components may be present in a homogeneous, storage stable mixture. Generally, calcium carbonate will be present in the cement in an amount ranging from about 5 to 25 wt. %, usually from about 5 to 20 wt. %, and more usually 10 to 20 wt. % of the entire weight of the dry components. The $\alpha$-tricalcium phosphate component will be present in an amount ranging from about 60 to 95 wt. %, usually from about 65 to 90 wt. % and more usually from about 70 to 90 wt. % of the entire weight of the dry components. Of particular interest for the $\alpha$-tricalcium phosphate is the reactive $\alpha$-tricalcium phosphate described in U.S. Pat. No. 5,569,442, the disclosure of which is herein incorporated by reference. The monocalcium phosphate monohydrate component will be present in an amount ranging from about 1 to 20 wt. %, usually from about 1 to 15 wt. % and more usually from about 2 to 15 wt. % of the entire weight of the dry components.

As described above, the cement will comprise a liquid component, e.g. setting solution or lubricant, in addition to the dry components described above. The setting solution or liquid may be water, either pure water or an aqueous composition comprising one or more different solutes in various concentrations. Preferably the setting solution will be a carbonate or phosphate containing solution at a pH in the range of 4 to 11, usually in the range of 6 to 11, preferably 7 to 9, wherein the concentration of carbonate or phosphate in the solution will preferably range from 0.05 to 0.5 molal (m), with a 0.05 to 0.1 molal (m) sodium phosphate solution (e.g. mono-, di- and tribasic sodium phosphate solution) being particularly preferred.

In addition to the above dry and liquid components, the cement will also comprise at least one, and usually no more than 3, more usually no more than two, antimicrobial agents, where the antimicrobial agent may be present in the liquid or dry component, but is preferably present in the liquid component, where it may be dissolved or dispersed in the liquid. Antimicrobial agents of interest include: Antiamebics, e.g. Arsthinol, Bialamicol, Carbarsone, Cephaeline, Chlorbetamide, Chloroquine, Chlorphenoxamide, Chlortetracycline, Dehydroemetine, Dibromopropamidine, Diloxanide, Diphetarsone, Emetine, Fumagillin, Glaucarubin, Glycobiarsol, 8-Hydroxy-7-iodo-5-quinoline-sulfonic Acid, Iodochlorhydroxyquin, Iodoquinol, Paromomycin, Phanquinone, Polybenzarsol, Propamidine, Quinfamide, Scenidazole, Sulfarside, Teclozan, Tetracycline, Thiocarbamizine, Thiocarbarsone, Tinidazole; Antibiotics, e.g. Aminoglycosides (such as Amikacin, Apramycin, Arbekacin, Bambermycins, Butirosin, Dibekacin, Dihydrostreptomycin, Fortimicin(s), Gentamicin, Isepamicin, Kaniamycin, Micronomicin, Neomycin, Neomycin Undecylenate, Netilmicin, Paromomycin, Ribostamycin, Sisomicin, Spectinomycin, Streptomycin, Tobramycin, Trospectomycin), Amphenicols (Azidamfenicol, Chloramphenicol, Florfenicol, Thiamphenicol), Ansamycins (Rifamide, Rifampin, Rifamycin, Rifapentine, Rifaximin), $\beta$-Lactams (Carbacephems, Loracarbef, Carbapenems (Biapenem, Imipenem, Meropenem, Panipenem), Cephalosporins (Cefaclor, Cefadroxil, Cefamandole, Cefatrizine, Cefazedone, Cefazolin, Cefcapene Povoxil, Cefclidin, Cefdinir, Cefditoren, Cefepime, Cefetamet, Cefixime, Cefinenoxine, Cefodizime, Cefonicid, Cefoperazone, Ceforanide, Cefotaxime, Cefotiam, Cefozopran, Cefpimizole, Cefpiramide, Cefpirome, Cefpodoxime Proxetil, Cefprozil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine, Pivcefalexin), Cephamycins (Cefbuperazone, Cefmetazole, Cefminox, Cefotetan, Cefoxitin), Monobactams (Aztreonam, Carumonam, Tigemonam), Oxacephens (Flomoxef, Moxalactam), Penicillins (Amdinocillin, Amdinocillin Pivoxil, Amoxicillin, Ampicillin, Apalcillin, Aspoxicillin, Azidocillin, Azlocillin, Bacampicillin, Benzylpenicillic Acid, Benzylpenicillin Sodium, Carbenicillin, Carindacillin, Clometocillin, Cloxacillin, Cyclacillin, Dicloxacillin, Epicillin, Fenbenicillin, Floxacillin, Hetacillin, Lenampicillin, Metampicillin, Methicillin Sodium, Mezlocillin, Nafcillin Sodium, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicllin V Benzathine, Penicillin V Hydrabamine, Penimepicycline, Phenethicillin Potassium, Piperacillin, Pivampicillin, Propicillin, Quinacillin, Sulbenicillin, Sultamicillin, Talampicillin, Temocillin, Ticarcillin), Ritipenem), Lincosamides (Clindamycin, Lincomycin), Macrolides (Azithromycin, Carbomycin, Clarithromycin, Dirithromycin, Erythromycin, Erythromycin Acistrate, Erythromycin Estolate, Erythromycin Glucoheptonate, Erythromycin Lactobionate, Erythromycin Propionate, Erythromycin Stearate, Josamycin, Leucomycins, Midecamycins, Miokamycin, Oleandomycin, Primycin, Rokitamycin, Rosaramicin, Roxithromycin, Spiramycin, Troleandomycin), Polypeptides (Amphomycin, Bacitracin, Capreomycin, Colistin, Enduracidin, Enviomycin, Fusafungine, Gramicidin S, Gramicidin(s), Mikamycin, Polymyxin, Pristinamycin, Ristocetin, Teicoplanin, Thiostrepton, Tuberactinomycin, Tyrocidine, Tyrothricin, Vancomycin, Viomycin, Virginiamycin, Zinc Bacitracin), Tetracyclines(Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Tetracycline), Cycloserine, Mupirocin, Tuberin; synthetic antibacterial agents, e.g. 2,4-Diaminopyrimidines (Brodimoprim, Textroxoprim, Trimethoprim), Nitrofurans (Furaltadone, Furazolium Chloride, Nifuradene, Nifuratel, Nifurfoline, Nifurpirinol, Nifurprazine, Nifurtoinol, Nitrofirantoin), Quinolones and Analogs (Cinoxacin, Ciprofloxacin, Clinafloxacin, Difloxacin, Enoxacin, Fleroxacin, Flumequine, Grepafloxacin, Lomefloxacin, Miloxacin, Nadifloxacin, Nadilixic Acid, Norflaxacin, Ofloxacin, Oxolinic Acid, Pazufloxacin, Pefloxacin, Pipemidic Acid, Piromidic Acid, Rosoxacin, Rufloxacin, Sparfloxacin, Temafloxacin, Tosufloxacin, Trovafloxacin), Sulfonamides (Acetyl Sulfamethoxpyrazine, Benzylsulfamide, Chloramine-B, Chloramine-T, Dichloramine T, $N^2$-Formylsulfisomidine, $N^4$-β-D-Glucosylsulfanilamide, Mafenide, 4'-(Methylsulfamoyl)sulfanilanilide, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine, Sulfisoxazole), Sulfones (Acedapsone, Acediasulfone, Acetosulfone Sodium, Dapsone, Diathymosulfone, Glucosulfone Sodium, Solasulfone, Succisulfone, Sulfanilic Acid, p-Sulfanilylbenzylamine, Sulfoxone Sodium, Thiazolsulfone), Clofoctol, Hexedine, Methenamine, Methenamine Anhydromethylenecitrate, Methenamine Hippurate, Methenamine Mandelate, Methenamine Sulfosalicylate, Nitroxoline, Taurolidine, Xibomol; leprostatic antibacterial agents, such as Acedapsone, Acetosulfone Sodium, Clofazimine, Dapsone, Diathymosulfone, Glucosulfone Sodium, Hydnocarpic Acid, Solasulfone, Succisulfone, Sulfoxone Sodium, antifungal agents, such as Allylamines Butenafine, Naftifine, Terbinafine, Imidazoles (e.g.Bifonazole, Butoconazole, Cholordantoin, Chlormidazole, Cloconazole, Clotrimazole, Econazole, Enilconazole, Fenticonazole, Flutrimazole, Isoconazole, Ketoconazole, Lanoconazole, Miconazole, Omoconazole, Oxiconazole Nitrate, Sertaconazole, Sulconazole, Tioconazole), Thiocarbamates (Tolcilate, Tolindate, Tolnaftate), Triazoles (Fluconazole, Itraconazole, Saperconazole, Terconazole), Acrisorcin, Amorolfine, Biphenamine, Bromosalicylchloranilide, Buclosamide, Calcium Propionate, Chlorphenesin, Ciclopirox, Cloxyquin, Coparaffinate, Diamthazole Dihydrochloride, Exalamide, Flucytosine, Halethazole, Hexetidine, Loflucarban, Nifuratel, Potassium Iodide, Propionic Acid, Pyrithione, Salicylanilide, Sodium Propionate, Sulbentine, Tenonitrozole, Triacetin, Ujothion, Undecylenic Acid, Zinc Propionate; and the like.

The amount of antimicrobial agent that is present in the cement will be sufficient to provide for a product that at least reduces the growth rate of microbial organisms in the region of the product as compared to a control. In many embodiments, the amount of antibiotic will be sufficient to provide for a zone of inhibition having a diameter of at least about 10 mm, usually at least about 15 mm, as measured by the antibiotic activity assay described in the Experimental Section, infra. As such, the amount of antimicrobial agent that is present in the cement will generally range from about 0.01 to 10, usually from about 0.01 to 5.0 and more usually from about 0.01 to 3.0% by weight of the dry ingredients of the cement. The amount of antimicrobial agent present in the cement will not be so great as to yield a product with a compressive strength that is substantially lower than the compressive strength of a control, where by substantially lower is meant at least about 50% lower.

In preparing the subject calcium phosphate cements for use in the subject methods, the dry components and the liquid components will be combined using any suitable means to produce a homogeneous, flowable paste-like material having the characteristics described above. One suitable means of combining the dry and liquid components is a mortar and pestle, with which the liquid and solid components are mixed to produce the flowable paste. Alternatively, one may employ an automated mixing device, as described in U.S. application Ser. No. 08/989,845, the disclosure of which is herein incorporated by reference.

The subject cements, paste-like compositions and products into which the paste-like compositions set find use in the local delivery of an antimicrobial agent, e.g. to a physiological site of interest. The subject compositions find use in such methods as they are capable of releasing antimicrobial agent into their local environment over an extended period of time, where the period of time is generally at least about 5, usually at least about 10 and more usually at least about 20 days, where the subject products may release the antimicrobial agent into their local environment for as long as 40 days or longer, depending on the specific cement from which the product is prepared. Thus, the subject compositions find use as extended antimicrobial agent delivery vehicles, i.e. as antimicrobial agent depots, in which the local delivery of an antimicrobial agent for an extended period of time is desired. The subject compositions find particular use as local antimicrobial agent delivery vehicles for bone tissue, particularly cancellous bone tissue.

Cements comprising the subject composite materials find use in a variety of dental, cranio maxillofacial and orthopedic applications. Representative applications in which the subject cements find use include those orthopedic, dental and cranio maxillofacial applications described in U.S. patent application Ser. No. 08/989,845 the disclosure of which is herein incorporated by reference.

Also provided are kits comprising the subject cements, where the dry and liquid components may be present in separate containers in the kit, or some of the components may be combined into one container, such as a kit wherein the dry components are present in a first container and the liquid components are present in a second container, where the containers may or may not be present in a combined configuration, as described in U.S patent application Ser. No. 08/989,845, the disclosure of which is herein incorporated by reference.

The following experiments are offered by way of illustration and not by way of limitation.

EXPERIMENTAL

I. Materials and Methods

The calcium phosphate cement used in this study was the Norian®SRS® Skeletal Repair System® calcium phosphate cement (Norian Corp., Cupertino, Calif.). A standard SRS kit consists of a calcium source powder (a mixture of tri-calcium phosphate and calcium carbonate), a phosphate source powder (monocalcium phosphate monohydrate) and a phosphate buffered solution component. The three components are mixed together in a mortar and pestle to form a paste-like material. The SRS cement hardens in vivo at physiological pH to form carbonated apatite with chemical and crystallographic characteristics similar to the mineral phase of bone. Vancomycin hydrochloride and gentamycin sulfate (Sigma Chemical, St. Louis Mo.) were added in powder form to the solution reactant of the SRS cement prior to mixing with the powder components. One percent gentamycin sulfate and one percent vancomycin hydrochloride by weight were tested in this experiment.

The material properties of the SRS cement with added antibiotics were evaluated using standardized ASTM test methods. Early strength attainment, injectability, and ultimate compressive strength were examined and compared with historical as well as internal control SRS cement specimens. Early strength attainment was evaluated by indentation testing. The indentation test utilizes circular rings of 2.5 cm I. D., and 5 mm thickness filled with the SRS cement so that a flat surface is obtained. Samples were cured for ten minutes at 37° C., removed from the incubator, and indented using an Instron testing machine set to a crosshead speed of 0.6 inches/minute and crosshead travel set to 0.05 inches. A Gilmore needle apparatus with a tip diameter of 5 mm is pressed into the sample 0.05 inches and the load required to push the needle this distance is measured. The ability to resist indentation at loads of 90 lbs or greater 10–12 minutes post mix is considered acceptable early strength attainment. Injectability was evaluated by measuring the load in pounds necessary to inject 5 cc of cement from a 10 cc syringe through a 12 gauge needle. Spike loads were measured using an Instron fitted with a test jig to hold the syringe in place as load is applied at the top of the syringe plunger at a crosshead speed of 2 inches/minute. This load is defined in the test not to exceed 15 lbs at 4 minutes post-mix for the cement to be termed injectable. Ultimate compressive strength was evaluated by filling cylindrical stainless steel dies 6 mm×12 mm with the cement paste and allowing the samples to harden 24 hours in bovine serum in a 37° C. humidified incubator for 24 hours. Samples were then removed from the die, placed on a steel platen and crushed at a crosshead speed of 0.1 inches/minute. Powder x-ray diffraction and carbon coulometry were used to determine relative crystallinity and carbonate content respectively. SRS cement samples with 1.0% gentamycin and 1.0% vancomycin by weight dissolved in the solution component were mixed and allowed to harden in phosphate buffered saline, pH=7.4 for 24 hours at 37° C. in a humidified incubator. Following incubation the samples were lyophilized to dryness, crushed, and ground to a fine powder in a mortar and pestle. Powder x-ray diffraction was performed on samples packed in aluminum sample holders, and scanned with a Phillips XRG 5000 fitted with a 42271/0 goniometer using copper k radiation. Samples were scanned over a 2θ range of 20° to 35° at a scan rate of 0.12°/minute and a step size of 0.01°. Carbonate content of the SRS cement specimens was performed with a carbon coulometer (Coulometrics, Joliet, Ill.) equipped with an acidification unit for carbon dioxide removal. This technique evolves carbon dioxide in acidic solution which reacts with a sensitive photometric indicator.

Fourier transform infrared spectroscopy (Nicolet model 510 spectrometer with NICOS software) was also performed on these samples. Lyophilized samples (10 mg) were dispersed in 300 mg dry potassium bromide and pressed into sample pellets. Fifty full spectrum sample scans were subtracted from 60 reference scans with no sample in the holder prior to Fourier transform. Scanning Electron Microscopy (SEM) was performed on the same SRS cement samples used for x-ray diffraction analyses described above. Lyophilized SRS cement samples were sputter coated with gold prior to microscopic analysis.

Release kinetics were examined through 44 days at 14 time intervals. Cement incorporated with 0.222 g Gentamycin (1% by weight) was placed in 50 ml of phosphate buffered saline (PBS), pH=7.4 and maintained at 37° C. A constant rotation stir motor agitated the solution. At each time period, the entire elute was removed and replaced with fresh PBS. Each elute was assayed for antibiotic concentration using a fluorescence immunoassay.

Activity of vancomycin and gentamycin was determined by the ability of hardened SRS cement with incorporated antibiotics to inhibit colony formation of Staphylococcus aureus, and Escherichia coli (Bacitrol disks, Difco Detroit, Mich.) when placed directly on top of confluent monolayer inoculated plates of Mueller-Hinton agar medium (Difco, Detroit Mich.). Zones of bacterial growth inhibition due to antibiotic susceptibility were compared with standardized disks containing antibiotic (10 µg gentamycin or 30 µg vancomycin, Difco, Detroit Mich.). Control SRS cement samples with no antibiotic served as negative controls. Antibiotic activity was also tested in the elutes from release rate studies at 1, 8, and 16 days. 25 µs and 100 µs of eluate at each of the three time periods were pipetted on the surface of streaked culture plates and allowed to dry in a laminar flow hood. Positive controls consisted of aliquots of PBS, pH=7.4, containing 200 µg/ml gentamycin sulfate (Sigma, St. Louis, Mo.) and negative controls were PBS alone.

Zones of bacterial growth inhibition due to antibiotic susceptibility of the eluted samples were compared with positive and negative controls to determine if the antibiotic was still active.

Statistical analysis was performed on early strength attainment, injectability, and ultimate compressive strength results by student t-tests.

II. Results

A. Early strength attainment

In control tests on SRS samples with no antibiotic, the maximum load of approximately 100 lbs. was reached at 10–12 minutes. One percent gentamycin added to the solution component prior to mixing delayed early strength attainment when compared to controls by an average of 3 minutes, as determined by indentation tests at 10–15 minutes post mix (n=13). However, at 14–16 minutes post-mix normal loads were seen with no significant difference compared to controls (Table 1). Dissolving vancomycin at 1% in the solution component did not affect early strength attainment (n=6).

TABLE 1

Rate of Strength Attainment of SRS with and without Antibiotic.

| Antibiotic (weight %) | Time post-mix (min.) | Indentation Load (lbs.) | p-value |
|---|---|---|---|
| 1.0% gentamycin sulfate | 10–12 | 22.70 ± 25.65 | 0.03* |
|  | 14–16 | 100.8 ± 1.18 | 0.55 |
| 1.0% vancomycin hydrochloride | 10–12 | 93.79 ± 18.92 | 0.38 |
| Control SRS | 10–12 | 101.2 ± 1.3 | N/A |

*p-value < 0.05

B. Ultimate compressive strength

Compression strengths were measured at 24 hours post mix after the SRS had hardened in bovine serum at 37° C. in a humidified incubator. Addition of one percent gentamycin or vancomycin to the solution component did not significantly affect the ultimate compressive strength. (Table 2)

TABLE 2

Ultimate Compressive Strength (24 hours) of SRS with and without Antibiotic.

| Antibiotic (weight %) | Compressive Strength (MPa) | p-value |
|---|---|---|
| Control SRS | 50.4 ± 4.5 | N/A |
| 1.0% Gentamycin sulfate | 47.0 ± 2.9 | 0.16 |
| 1.0% Vancomycin hydrochloride | 45.4 ± 4.1 | 0.08 |

C. Injectability

In control tests of SRS alone, injection spike load and the load required to inject 1 ml were less than 15 lbs. Addition of 1.0% gentamycin or 1.0% vancomycin to the solution component did not significantly increase the spike load when compared to controls nor did the antibiotics significantly increase the load required to inject 1 ml. Injectability, as indicated by the load required to inject 3 cc of SRS was evaluated at 90 seconds and 4 minutes post-mix. SRS remained injectable after addition of both gentamycin and vancomycin at both time periods. All samples required less than 15 lbs load applied at the syringe plunger for injection (n=12). (See Table 3)

The deliverable dose in the control data was approximately 3 cc. Neither antibiotic significantly affected the deliverable dose of SRS (see Table 3).

TABLE 3

Injectability of Norian SRS with and without Antibiotic.

| Antibiotic (weight %) | Spike Load (lbs.) | 1 ml Injection Load (lbs.) | Deliverable Dose (ml) |
|---|---|---|---|
| 1.0% Gentamycin sulfate | 10.2 ± 0.8* | 13.2 ± 0.3 | 3.0 ± 0.6 |
| 1.0% Vancomycin hydrochloride | 11.8 ± 1.8 | 13.0 ± 1.0 | 2.7 ± 0.2 |
| Control SRS | 13.7 ± 0.8 | 13.8 ± 0.6 | 2.8 ± 0.5 |

*p-value < 0.05

D. Release kinetics

The elution kinetics of gentamycin (1.0 weight percent) from SRS were examined over a 44 day time period. Release rates were calculated for short term (15 min), near term (1–24 hrs) and long term (2–44 days) intervals. The results showed a rapid release of gentamycin (~80 $\mu$g/min) from the cement over the first 15 minutes followed by a leveling to an average of 0.5 $\mu$g/min over the remaining 44 days. The cumulative amount of gentamycin released at various time periods through the 44 day study period are shown in FIG. 1. The total amount of gentamycin incorporated in the cement was 0.222 g and the total released over the 44 day time period was 0.025 grams (9% released). These data suggest that the eluate around the SRS cement containing gentamycin are at similar concentrations to the minimum inhibitory concentration for *Staphylococcus aureus* (0.5–2.0 $\mu$g/ml).

E. Antibiotic Activity

The antibacterial activity of gentamycin and vancomycin eluted from the SRS cement was examined using antibiotic incorporated cement samples which had been cured for 24 hours in PBS. Hardened SRS cement samples were placed on the surface of Mueller-Hinton agar plates previously inoculated to produce confluent monolayers of *Staphylococcus aureus*. Positive control disks produced zones of inhibition to *Staphylococcus aureus* growth having diameters greater than 15 mm suggesting susceptibility (Table 4). One percent gentamycin produced greater than 15 mm zones of bacterial growth inhibition suggesting susceptibility to active antibiotic. Positive control paper disks containing 10 $\mu$g gentamycin produced growth inhibition zones of 18.9±1.3 mm (n=7). Negative control cement samples and paper disks with no antibiotic showed no growth inhibition. Gentamycin loaded SRS produced growth inhibition zones greater than or equal to positive controls (n=28). Vancomycin at 1% by weight resulted in greater than 15 mm zones of bacterial growth inhibition suggesting susceptibility to active antibiotic. (See Table 4)

Eluates from the release rate studies were also tested for gentamycin activity. 25 $\mu$L and 100 $\mu$L aliquots from 1, 8, and 16 day intervals were assayed by pippetting the sample on to the surface of agar/Mueller-Hinton plates previously inoculated with *E. coli*. Zones of growth inhibition were compared with positive control paper disks containing 10 $\mu$g gentamycin and positive control PBS solutions containing 200 $\mu$g/ml gentamycin. Zones of growth inhibition greater than positive control disks were observed with all eluate samples tested for each time interval suggesting susceptibility to active antibiotic. Negative controls of PBS showed no growth inhibition. (See Table 5.)

TABLE 4

Susceptibility of *Staphylococcus aureus* to SRS Specimens with Antibiotic.

| Specimen | Zone of Inhibition (mm) |
| --- | --- |
| SRS alone (Negative control) | 0 |
| 1.0% Gentamycin SRS | 19.6 ± 4.6 |
| Gentamycin disk (Positive control) | 18.9 ± 1.3 |
| 1% Vancomycin SRS | 18.9 ± 1.1 |
| Vancomycin disk (Positive control) | 16.3 ± 1.9 |

TABLE 5

Susceptibility of *E. coli* to Gentamycin Eluates at 1, 8, 16 days. Growth inhibition zones. (GIZ mm)

| Day # | 25 μL of eluate from 1% Gentamycin SRS (GIZ mm) | 25 μL of 200 μg/mL Gentamycin in PBS (Positive control)(GIZ mm) | 25 μL PBS pH = 7.4 No antibiotic (Negative control) (GIZ mm) | 10 μg Gentamycin loaded paper disk (Positive control) (GIZ mm) |
| --- | --- | --- | --- | --- |
| 1 | 20 | 18 | 0 | 21 |
| 8 | 7 | 16 | 0 | 20 |
| 16 | 12 | 16 | 0 | 14 |

F. Mineralogy

Figure 2A:
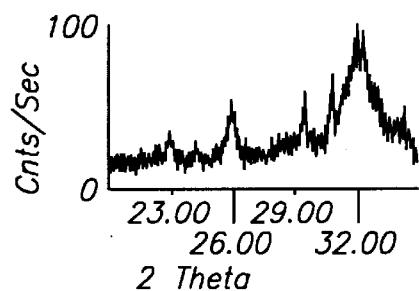
FIG. 2 provides X-ray diffraction patterns of a control calcium phosphate cement (A), a calcium phosphate cement loaded with 1% Gentamycin (B), and a calcium phosphate cement loaded with 1% Vancomycin (C). No detectable difference in apatite mineral phase is apparent.
Figure 2B:
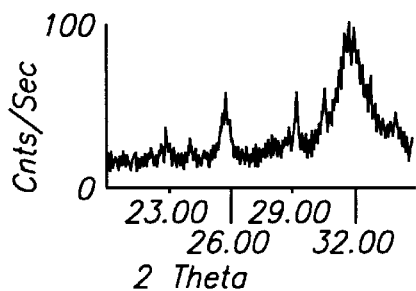
Figure 2C:
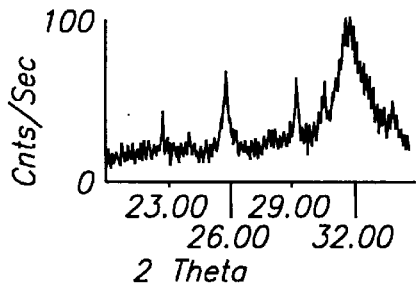
Figure 3A:
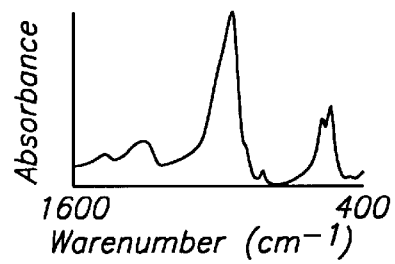
FIG. 3 provides Fourier Transformed Infrared Spectra of a control calcium phosphate cement(A), a calcium phosphate cement with 1% Gentamycin (B), a calcium phosphate cement with 1% Vancomycin (C). All spectra are indicative of carbonated apatite (dahllite).
Figure 3B:
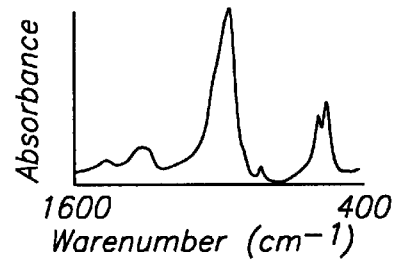
Figure 3C:
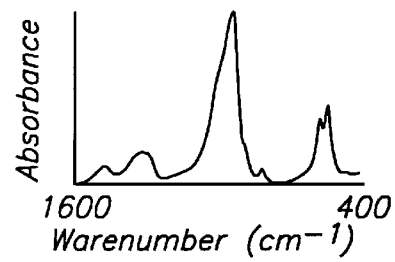

No detectable difference in crystalline order, bulk carbonate content, or microstructure was observed for the addition of the two antibiotics. XRD and FTIR patterns are provided in FIGS. 2 and 3 respectively for control SRS cement, SRS cement with additions of 1.0% gentamycin sulfate, and SRS cement with the addition of 1.0% vancomycin hydrochloride. Carbonate content of control SRS cement, 1% gentamycin and 1% vancomycin specimens, was 5.4, 4.9, and 5.3 weight percent respectively. These values are within the 4–6 weight percent carbonate content previously reported for SRS cement and dahllite, the mineral phase of bone.

It is apparent from the above results and discussion that calcium phosphate cements capable of being used as delivery vehicles for therapeutic doses of antibiotic are provided. The subject calcium phosphate cements are particularly useful in the introduction of antibiotics into bone tissue, particularly cancellous bone tissue, as they set into antimicrobial agent loaded apatitic products with sufficient compressive strengths to withstand compressive forces experienced by cancellous bone under normal physiological conditions.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A calcium phosphate cement, said cement comprising:
   dry ingredients comprising α-tricalcium phosphate in an amount ranging from about 60 to 95 wt. % of said dry ingredients; monocalcium phosphate monohydrate in an amount ranging from about 1 to 20 wt. % of said dry ingredients and calcium carbonate in an amount ranging from about 5 to 25 wt. % of said dry ingredients;
   a physiologically acceptable aqueous lubricant in an amount sufficient to produce a flowable product upon combination with said dry ingredients; and
   an antimicrobial agent in an amount ranging from about 0.01 to 10 wt. % of said dry ingredients;
   wherein when said components are combined, a flowable product is produced that sets in less than about 20 minutes into an apatitic product having a compressive strength of at least about 40 MPa.

2. The cement according to claim 1, wherein said physiologically acceptable aqueous lubricant comprises a sodium phosphate.

3. The cement according to claim 2, wherein said physiologically acceptable aqueous lubricant has a pH ranging from about 4 to 11.

4. The cement according to claim 2, wherein the concentration of said sodium phosphate in said physiologically acceptable aqueous lubricant ranges from about 0.05 to 0.5 molal.

5. The cement according to claim 1, wherein said antimicrobial agent component is present in said physiologically acceptable aqueous lubricant.

6. A calcium phosphate cement, said cement comprising:
   dry ingredients comprising α-tricalcium phosphate in an amount ranging from about 60 to 95 wt. % of said dry ingredients, monocalcium phosphate monohydrate in an amount ranging from about 1 to 20 wt. % of said dry ingredients and calcium carbonate in an amount ranging from about 5 to 25 wt. % of said dry ingredients;
   a sodium phosphate buffer solution in an amount sufficient to produce a flowable product upon combination with said dry ingredients; and
   an antimicrobial agent in an amount ranging from about 0.01 to 10 wt. % of said dry ingredients;
   wherein when said components are combined, a flowable product is produced that sets in less than about 15 minutes into an apatitic product having a compressive strength of at least about 40 MPa.

7. The cement according to claim 6, wherein said α-tricalcium phosphate is reactive α-tricalcium phosphate.

8. The cement according to claim 6, wherein said antimicrobial agent is present in an amount ranging from about 0.01 to 3.0% w/w.

9. The cement according to claim 6, wherein said antimicrobial agent is present in said buffer solution.

10. The cement according to claim 6, wherein said sodium phosphate buffer solution has a pH ranging from about 4 to 11.

11. A calcium phosphate cement, said cement comprising:

dry ingredients comprising reactive α-tricalcium phosphate in an amount ranging from about 60 to 95 wt. % of said dry ingredients, monocalcium phosphate monohydrate in an amount ranging from about 1 to 20 wt. % of said dry ingredients and calcium carbonate in an amount ranging from about 5 to 25 wt. % of said dry ingredients; and a sodium phosphate buffer solution comprising an antimicrobial agent in an amount ranging from about 0.1 to 3% w/w of said dry ingredients;

wherein when said components are combined, a flowable product is produced that sets in less than about 15 minutes into an apatitic product having a compressive strength of at least about 40 MPa.

12. The cement according to claim 11, wherein said antimicrobial agent is selected from the group consisting of gentamycin and vancomycin.

13. A flowable composition that sets in less than about 20 minutes into an antimicrobial agent loaded apatitic product having a compressive strength of at least about 40 MPa, wherein said composition is prepared by:

(a) combining:
  (1) dry ingredients comprising α-tricalcium phosphate in an amount ranging from about 60 to 95 wt. % of said dry ingredients; monocalcium phosphate monohydrate in an amount ranging from about 1 to 20 wt. % of said dry ingredients and calcium carbonate in an amount ranging from about 5 to 25 wt. % of said dry ingredients;
  (2) a physiologically acceptable aqueous lubricant in an amount sufficient to produce a flowable product upon combination with said dry ingredients; and
  (3) an antimicrobial agent agent in an amount ranging from about 0.01 to 10 wt. % of said dry ingredients; and (b) mixing said combined components in a manner sufficient to produce said flowable composition.

14. The flowable composition according to claim 13, wherein said dry ingredients further comprise at least one additional calcium source.

15. The flowable composition according to claim 13, wherein said physiologically acceptable aqueous lubricant is a sodium phosphate buffer solution.

16. The flowable composition according to claim 13, wherein said antimicrobial agent is present in said physiologically acceptable aqueous lubricant.

17. The flowable composition according to claim 13, wherein said composition sets into said antimicrobial agent loaded apatitic product in less than 10 minutes.

18. A method of preparing a flowable composition that sets in less than about 20 minutes into an antimicrobial agent loaded product having a compressive strength of at least about 40 MPa, said method comprising:

(a) combining:
  (1) dry ingredients comprising α-tricalcium phosphate in an amount ranging from about 60 to 95 wt. % of said dry ingredients; monocalcium phosphate monohydrate in an amount ranging from about 1 to 20 wt. % of said dry ingredients and calcium carbonate in an amount ranging from about 5 to 25 wt. % of said dry ingredients;
  (2) a a physiologically acceptable aqueous lubricant in an amount sufficient to produce a flowable product upon combination with said dry ingredients; and
  (3) an antimicrobial agent in an amount ranging from about 0.01 to 10 wt. % of said dry ingredients; and (b) mixing said combined components in a manner sufficient to produce said flowable composition that sets in less than about 20 minutes into an antimicrobial agent loaded product having a compressive strength of at least about 40 MPa.

19. The method according to claim 18, wherein said physiologically acceptable aqueous lubricant is a sodium phosphate buffer solution.

20. The method according to claim 18, wherein said antimicrobial agent is selected from the group consisting of gentamycin and vancomycin.

21. A kit for use in preparing a flowable composition that sets in less than about 20 minutes into an antimicrobial agent loaded product having a compressive strength of at least about 40 MPa, said kit comprising:

dry ingredients comprising α-tricalcium phosphate in an amount ranging from about 60 to 95 wt. % of said dry ingredients; monocalcium phosphate monohydrate in an amount ranging from about 1 to 20 wt. % of said dry ingredients and calcium carbonate in an amount ranging from about 5 to 25 wt. % of said dry ingredients;

a physiologically acceptable aqueous lubricant in an amount sufficient to produce a flowable product upon combination with said dry ingredients; and an antimicrobial agent in an amount ranging from about 0.01 to 10 wt. % of said dry ingredients.

22. The kit according to claim 21, wherein said α-tricalcium phosphate is present in amount ranging from about 65 to 90 wt. % of said dry ingredients.

23. The kit according to claim 22, wherein said α-tricalcium phosphate is reactive α-tricalcium phosphate.

24. The kit according to claim 21, wherein said monocalcium phosphate monohydrate is present in an amount ranging from about 1 to 15 wt. % of said dry ingredients.

25. The kit according to claim 21, wherein said calcium carbonate is present in an amount ranging from about 5 to 20 wt. % of said dry ingredients.

26. The kit according to claim 21, wherein said physiologically acceptable aqueous lubricant is a sodium phosphate buffer solution.

27. The kit according to claim 26, wherein said sodium phosphate buffer solution has a pH ranging from about 4 to 11.

28. The kit according to claim 21, wherein said antimicrobial agents are selected from the group consisting of gentamycin and vancomycin.

29. In a method of bone repair in which a calcium phosphate cement composition is introduced into a bone repair site, the improvement comprising:

introducing the flowable composition according to claim 13 into said bone repair site.

* * * * *